United States Patent [19]
Eggers

[11] Patent Number: 5,391,166
[45] Date of Patent: Feb. 21, 1995

[54] BI-POLAR ELECTROSURGICAL ENDOSCOPIC INSTRUMENTS HAVING A DETACHABLE WORKING END

[75] Inventor: Philip E. Eggers, Dublin, Ohio

[73] Assignee: Hemostatic Surgery Corporation, Grand Cayman, Cayman Islands

[21] Appl. No.: 959,046

[22] Filed: Oct. 9, 1992

Related U.S. Application Data

[63] Continuation-in-part of Ser. No. 877,704, May 1, 1992, Pat. No. 5,330,471, which is a continuation-in-part of Ser. No. 711,920, Jun. 7, 1991, abandoned.

[51] Int. Cl.⁶ ............................................. A61B 17/38
[52] U.S. Cl. ........................................ 606/48; 606/32; 606/34; 606/37; 606/39; 606/40; 606/49; 606/170; 606/174; 606/207
[58] Field of Search ............... 606/32, 34, 37, 39, 606/40-41, 48-52, 170, 174, 110-112, 207; 128/399, 402

[56] References Cited

U.S. PATENT DOCUMENTS

| | | |
|---|---|---|
| 659,409 | 9/1900 | Mosher . |
| 1,586,645 | 6/1926 | Bierman . |
| 1,798,902 | 3/1931 | Raney . |
| 3,651,811 | 3/1972 | Hildebrandt ................. 606/51 |
| 4,128,099 | 12/1978 | Bauer . |
| 4,232,676 | 11/1980 | Herczog . |
| 4,353,371 | 10/1982 | Cosman . |
| 4,370,980 | 2/1983 | Lottick . |
| 4,643,190 | 2/1987 | Heimberger . |
| 4,655,216 | 4/1987 | Tischer . |
| 4,657,016 | 4/1987 | Garito et al. ................. 606/51 |
| 4,669,471 | 6/1987 | Hayashi . |
| 4,671,274 | 6/1987 | Sorochenko . |
| 4,754,754 | 7/1988 | Garito et al. ................. 606/49 |
| 4,763,669 | 8/1988 | Jaeger . |
| 4,785,807 | 11/1988 | Blanch . |
| 4,819,633 | 4/1989 | Bauer et al. . |
| 4,848,337 | 7/1989 | Shaw et al. . |
| 4,887,612 | 12/1989 | Esser et al. . |
| 4,944,093 | 7/1990 | Falk . |
| 4,950,273 | 8/1990 | Briggs ......................... 606/174 |
| 4,977,900 | 12/1990 | Fehling et al. . |
| 4,985,030 | 1/1991 | Melzer et al. . |
| 5,009,656 | 4/1991 | Reimels . |
| 5,085,659 | 2/1992 | Rydell . |
| 5,133,736 | 7/1992 | Bales, Jr. et al. ............ 606/170 |
| 5,147,357 | 9/1992 | Rose et al. . |
| 5,192,280 | 3/1993 | Parins ........................... 606/48 |
| 5,196,009 | 3/1993 | Kirwan, Jr. .................. 606/52 |
| 5,261,918 | 11/1993 | Phillips et al. ................ 606/41 |

FOREIGN PATENT DOCUMENTS

| | | | |
|---|---|---|---|
| 2355521 | 1/1978 | France ........................... 606/52 |
| 2037167 | 7/1980 | United Kingdom ......... 606/50 |
| 342619 | 7/1971 | U.S.S.R. . |
| 575103 | 10/1977 | U.S.S.R. . |

OTHER PUBLICATIONS

Corson, S. L., "Two new laparoscopic instruments: Bipolar sterilizing forceps and uterine manipulator," *Medical Instrumentation*, vol. 1, No. 11, Jan.–Feb. 1977.
The Lancet, "New Inventions", Oct. 24, 1959, J. D. K. Burton, pp. 650-651.

*Primary Examiner*—Randall L. Green
*Assistant Examiner*—P. Zuttarelli
*Attorney, Agent, or Firm*—Fish & Neave; Nicola A. Pisano

[57] ABSTRACT

Endoscopic surgical instruments are provided that have detachable working ends for use with a reusable handle portion. The detachable working end includes bipolar electrodes on opposing movable members for passing a high frequency current through tissue for simultaneously severing or manipulating the tissue and causing hemostasis of the tissue. An electrically insulating material is interposed between the movable members so that the electrodes are spaced apart from 0.002 to 0.050 inches and the current passes between the opposing electrodes through the tissue.

31 Claims, 12 Drawing Sheets

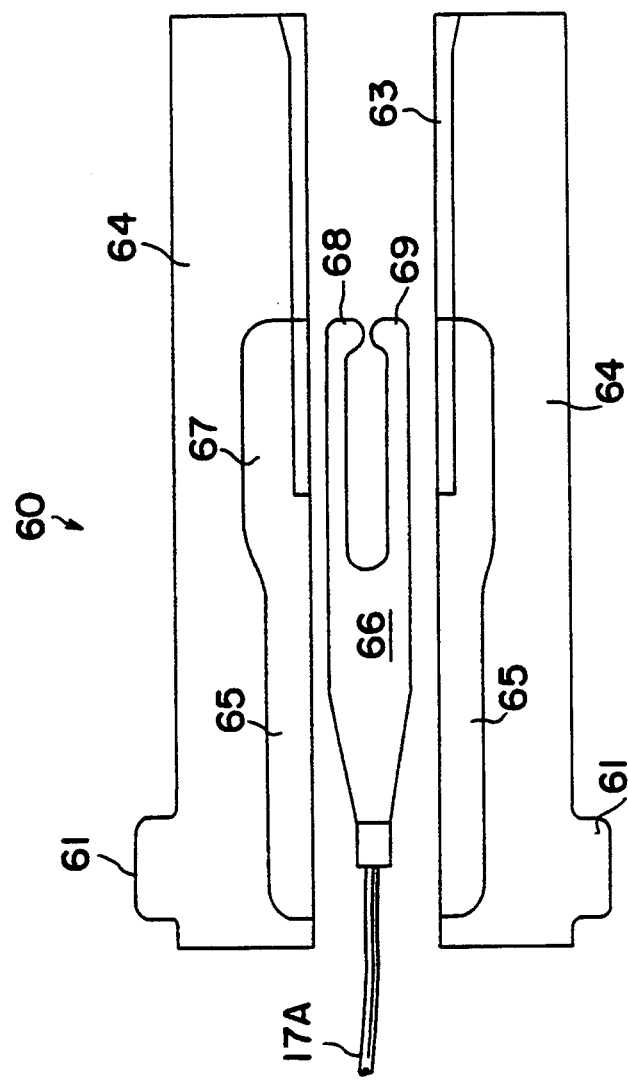

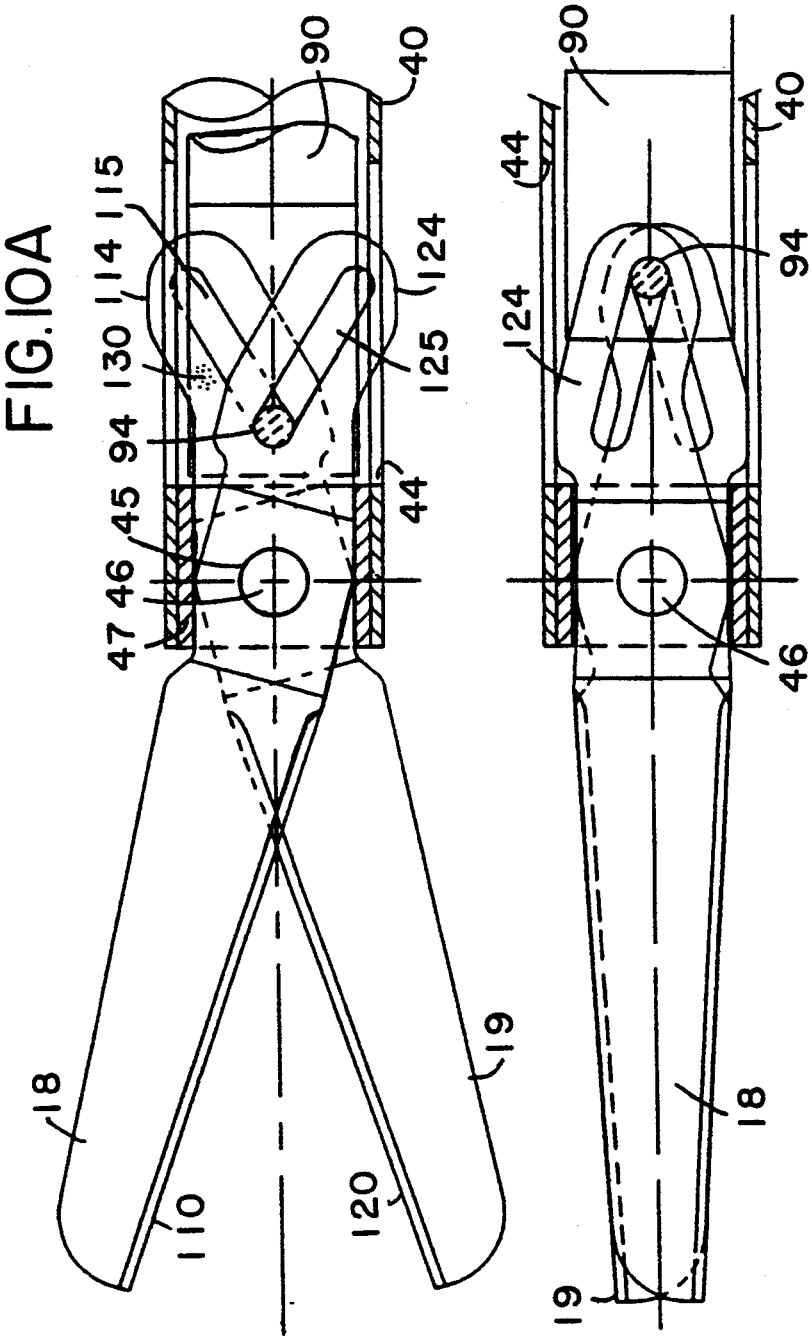

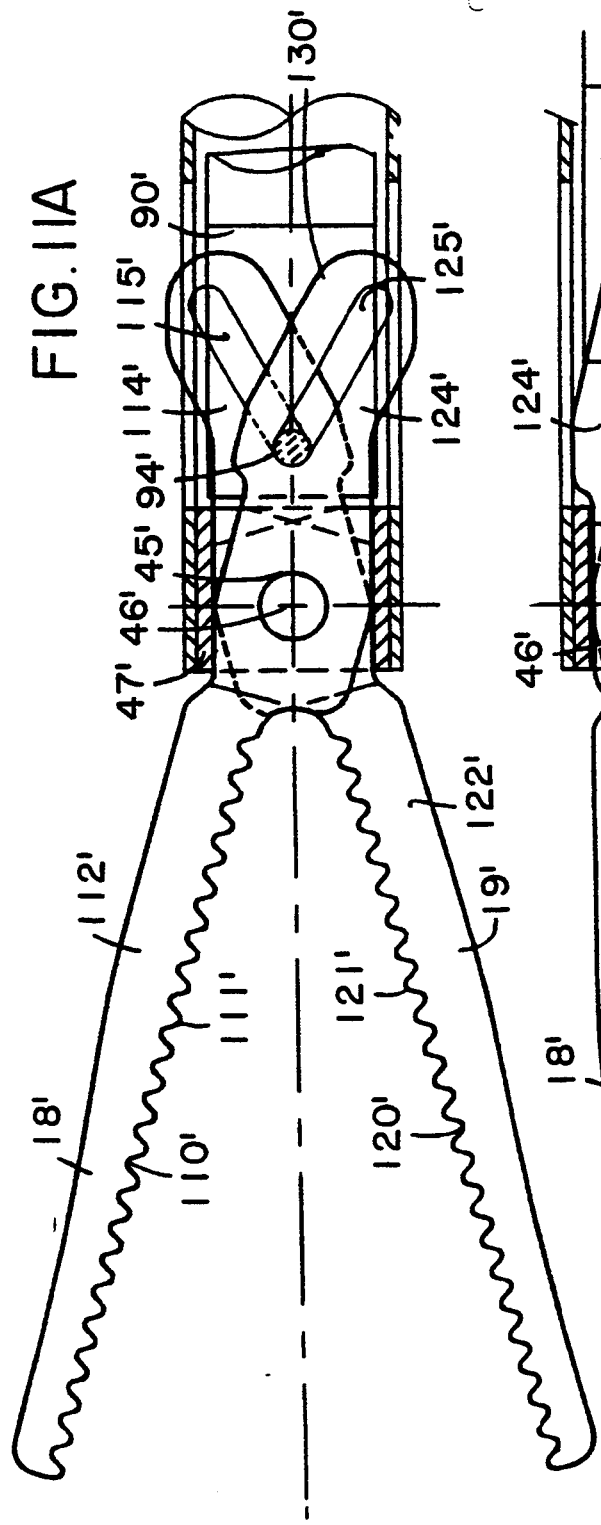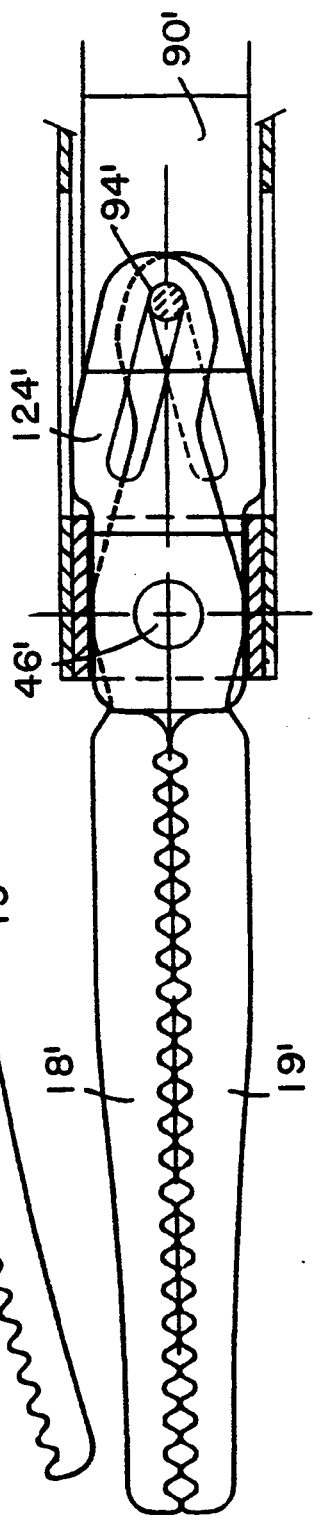

BI-POLAR ELECTROSURGICAL ENDOSCOPIC INSTRUMENTS HAVING A DETACHABLE WORKING END

CROSS REFERENCE TO RELATED APPLICATIONS

This application is a continuation-in-part of commonly assigned U.S. patent application Ser. No. 07/877,704, now U.S. Pat. No. 5,330,471, filed May 1, 1992, which is a continuation in part of U.S. patent application Ser. No. 07/711,920, filed Jun. 7, 1991, now abandoned.

This invention relates to hemostatic electrosurgical instruments, and particularly to improved bi-polar electrosurgical instruments having a detachable working end for manipulating and causing hemostasis of tissue during endoscopic surgical procedures.

BACKGROUND OF THE INVENTION

Bipolar hemostatic endoscopic instruments are described in my copending and commonly assigned U.S. patent application Ser. No. 07/877,704 now U.S. Pat. No. 5,330,471. The devices described in that application, which is incorporated herein by reference, overcome the disadvantages of previously known devices by providing bipolar electrosurgical instruments having electrically isolated electrodes.

The electrodes at the working end of these instruments may become worn through repeated use, and the surface finishes of the components may deteriorate due to repeated sterilization in conventional high-temperature steam autoclaves. Thus, it would be desirable to provide a bipolar endoscopic instrument having detachable working ends that may be replaceably connected to a reusable handle portion.

In addition, since the need may arise during surgery to employ working ends having different configurations, for example, curved shears instead of straight-edge shears, it would be desirable to provide a bipolar endoscopic instrument having a reusable handle portion with which differently configured working ends may be removably engaged.

SUMMARY OF THE INVENTION

In view of the foregoing, the present invention represents an improvement of the bipolar hemostatic endoscopic instruments described in the foregoing application, by providing detachable and interchangeable working ends. It is therefore an object of the present invention to provide improved endoscopic surgical instruments that have a simple structure, yet provide the necessary electrical isolation of the bipolar electrodes. The bipolar devices constructed in accordance with the present invention confine current flow to the tissue immediately adjacent to the electrodes of the instrument.

It is another object of this invention to provide bipolar electrosurgical instruments that have detachable working ends, so that worn working ends may be replaced.

It is another object of the present invention to provide bipolar electrosurgical instruments having reusable handle portions and detachable working ends, so that the working end may be easily detached and replaced by a differently configured working end.

These and other objects are accomplished in accordance with the principles of the present invention by providing bipolar electrosurgical instruments having a reusable handle portion comprising an elongated barrel for insertion through a trocar tube at the patient's skin and handle members for actuating the instrument, and a detachable working end disposed on the distal end of the elongated barrel. Engagement means are provided for removably connecting the working end to the distal end of the elongated barrel. The instrument includes means for connecting the instrument to a power supply to energize bipolar electrodes at the working end.

Bipolar instruments constructed in accordance with the present invention have a detachable working end that comprises bipolar electrodes and movable members capable of performing any of a number of functions. A layer of insulation is provided on one or both of the mating surfaces of the movable members to maintain electrical isolation of those components. A working end constructed in accordance with the present invention may comprise a scissors-like cutting instrument which simultaneously causes hemostasis of tissue and mechanically severs that tissue in a continuous manner, a dissector-like instrument for grasping and achieving hemostasis of tissue, or a dissector for blunt dissection, which hemostatically separates tissue, any of which may be interchangeably used with the reusable handle portion.

In a first embodiment of the detachable working end, the movable members of the working end comprise scissor members having opposing mating surfaces. Electrodes associated with the scissor members conduct high frequency current to tissue to coagulate the blood vessels extending through the tissue while cutting edges of the scissor members mechanically sever the tissue. A layer of insulating material is disposed on at least one of the mating surfaces of the scissor members so that the electrically active portions of the scissor members do not contact each other at any point during operation of the instrument. Thus, current flows through tissue between the scissor members, but short circuits, which would terminate hemostasis, do not occur. With this arrangement, hemostasis and cutting occurs in a continuous manner along tissue disposed between the scissor members, thereby providing a smooth and precise surgical cut.

Another embodiment of the invention comprises an endoscopic hemostatic dissector, wherein the movable members comprise opposing jaws for simultaneously grasping and causing hemostasis of the tissue. Like the first embodiment, the jaw members include shank portions forming opposing mating surfaces. A layer of insulating material is disposed on at least one of these mating surfaces so that electrically active portions of the members do not contact each other during operation of the instrument.

The movable members of either working end embodiment may be curved so that the tips of the members lie in a plane parallel to, and separate from, the longitudinal axis of the elongated barrel. This feature enhances the surgeon's view of the working end of the instrument, thereby providing greater precision in manipulating the tissue at the operative site.

BRIEF DESCRIPTION OF THE DRAWINGS

The above and other objects and advantages of the invention will be apparent upon consideration of the following detailed description, taken in conjunction with the accompanying drawings, in which like reference numerals refer to like parts throughout, and in which:

FIGS. 5A and 5B are exploded side and end elevation views of insulator block 50 of FIG. 4;

FIGS. 10A and 10B show, respectively, open and closed enlarged cross-sectional views of the detachable working end of the instrument shown in FIG. 3A; and FIGS. 11A and 11B, respectively, are cross-sectional views, similar to FIGS. 10A and 10B, showing a dissector embodiment of the working end of the present invention.

DETAILED DESCRIPTION OF THE INVENTION

Figure 1:
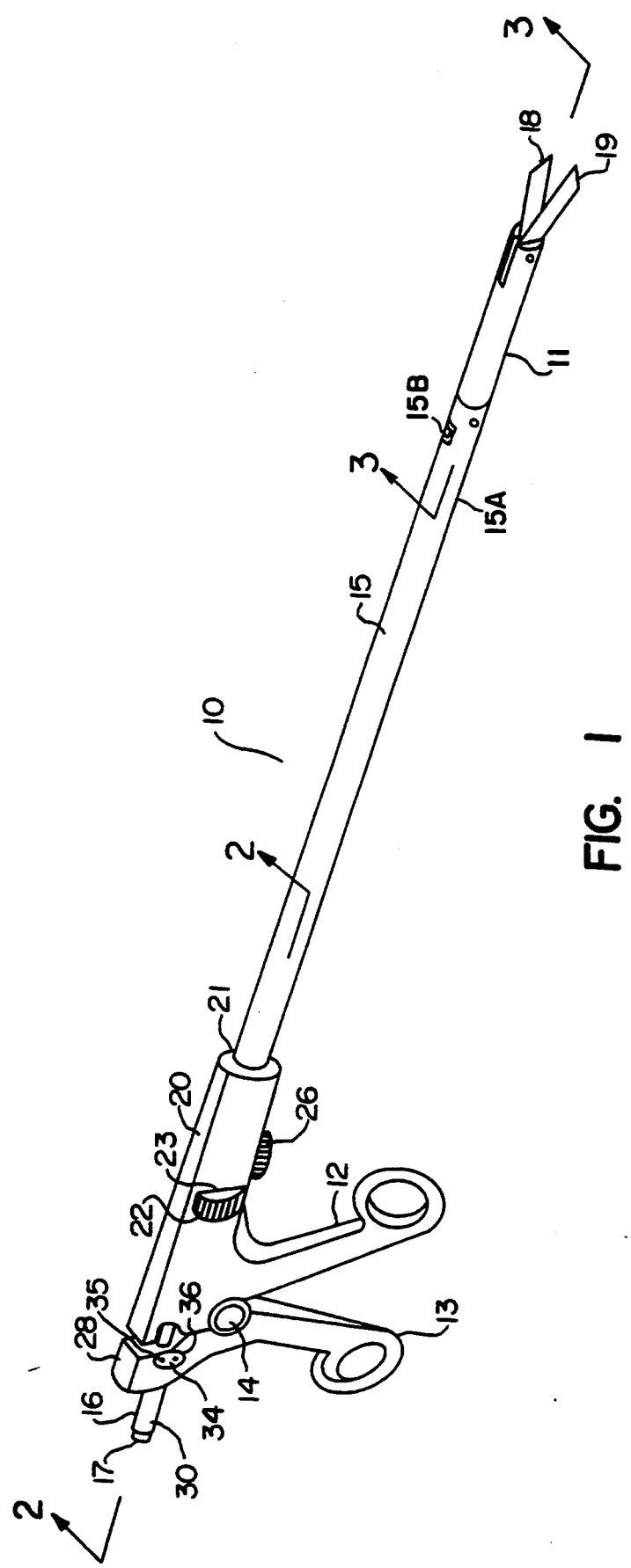
FIG. 1 is an elevated perspective view of an illustrative embodiment of the instrument of the present invention.
Figure 2:
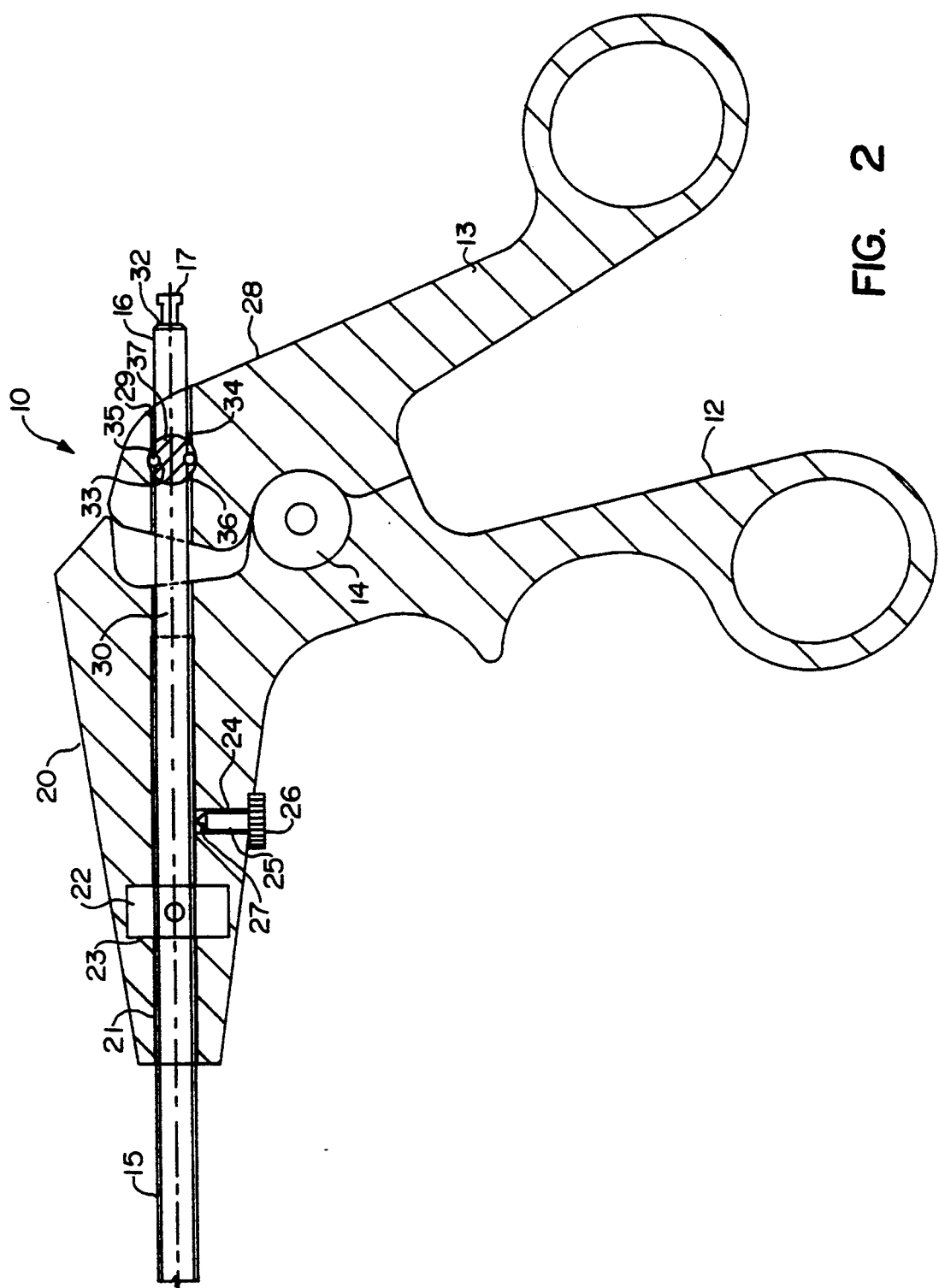
FIG. 2 is an elevation cross-sectional partial side view of the instrument taken along the line 2—2 of FIG. 1.

Referring to FIGS. 1 and 2, a bipolar electrosurgical instrument 10 for performing endoscopic surgical procedures is described. While an instrument constructed in accordance with the principles of the present invention may include any of a variety of severing or grasping members at its working end 11, the illustrative embodiment of FIGS. 1 and 2 includes scissor-like shearing members for simultaneously severing and causing hemostasis of a patient's tissue.

Instrument 10 includes a reusable handle portion comprising handle members 12, 13 joined for relative movement at pivot 14, and tubular elongated barrel 15, and detachable working end 11. Drive rod 16 disposed in elongated barrel 15 has electrical terminals 17 that are connected to movable members 18 and 19 of working end 11 to provide an electrical potential therebetween.

Handle member 12 has a pistol-like configuration, including a body portion 20 having a longitudinal bore 21 and a portion defining a hole for one or more fingers. Handle member 12 may be made of a light-weight rigid material, for example cast aluminum or cast zinc alloy. Elongated barrel 15 comprises a tube having a proximal end mounted in body portion 20 and a distal portion 15A adapted to receive working end 11. The proximal end of elongated barrel 15 is mounted in bore 21 of body portion 20 so that elongated barrel 15 can be rotated about its longitudinal axis. Elongated barrel may consist of a rigid structural material, for example a stainless steel alloy, e.g., SS 304, and may include a coating or sleeve of a low friction, low reflectance material, such as Teflon, on its exterior surface.

Knurled rotation knob 22 is mounted on a portion of elongated barrel 15 disposed in body portion 21, so that it projects through slots 23 intersecting bore 21 of body portion 20. Rotation of knurled knob 22 causes elongated barrel 15 to rotate about its longitudinal axis, thereby also rotating detachable working end 11.

Body member 20 may have bore 24 communicating with bore 21 so that set screw 25 disposed in bore 24 engages elongated barrel 15 substantially perpendicularly to the longitudinal axis of the barrel. Set screw 25 has locking knob 26 at one end and teat 27 at the other end to engage elongated barrel 15. Rotation of locking knob 26 may impose a load on elongated barrel 15 to establish a threshold torque for rotating knurled rotation knob 22. Alternatively, locking knob 26 may be rotated so that teat 27 of set screw 25 effectively locks elongated barrel 15 in a given angular orientation, and against further rotation.

Handle member 13 has a lower portion defining a finger or thumb hole and an upper portion 28 having longitudinal bore 29. Longitudinal bore 29 aligns with longitudinal bore 21 in body portion 20 of handle member 12 when handle members 12 and 13 are joined for relative movement at pivot 14. Handle member 13 comprises a similar material as handle member 12, e.g., a cast aluminum alloy.

Drive rod 16 comprises an electrically non-conducting sturdy rod, having a central bore (not shown) and comprised, for example, of polyaryletheretherkeytone, also known as "PEEK", available from ICI (U.K.), BASF and DuPont. Drive rod 16 has a proximal end 30 disposed within elongated barrel 15 and a distal end adapted to engage with working end 11 as described hereinafter. Proximal end 30 of drive rod 16 has electrical terminals 17 projecting from its endface 32, and may include a portion adjacent to its proximal endface 32 that defines a semi-circular groove 33. Electrical leads disposed in the central bore of drive rod 16 connect electrical terminals 17 to the detachable working end.

Groove 33 of drive rod 16 is captured in disk 34 between pins 35. Disk 34 seats in circular aperture 36 in upper portion 28 of handle member 13. Disk 34 may comprise a high strength plastic, such as, Ultem (a proprietary plastic of the General Electric Company, Fort Wayne, Ind., fabricated from polyetherimide), or a ceramic material. Longitudinal bore 37 extends through disk 34 in alignment with longitudinal bore 29 of upper portion 28, for accepting proximal portion 30 of drive rod 16. Disk 34 includes a pair of bores that perpendicularly intersect bore 37, the pair of bores accepting retaining pins 35. Disk 34 is capable of angular movement in circular aperture 36 when handle member 13 rotates relative to handle member 12 about pivot 14.

Retaining pins 35, which may comprise a sturdy material such as ceramic or anodized aluminum, engage groove 33 in drive rod 16 so that the drive rod 16 is capable of rotating about its longitudinal axis, but cannot move transversely with respect to retaining pins 35. Accordingly, drive rod 16 is mounted to handle member 13 for rotation about its longitudinal axis in retaining pins 35 and for transverse motion with respect to handle member 12 by virtue of angular movement of disk 34 in aperture 36.

Figure 3A:
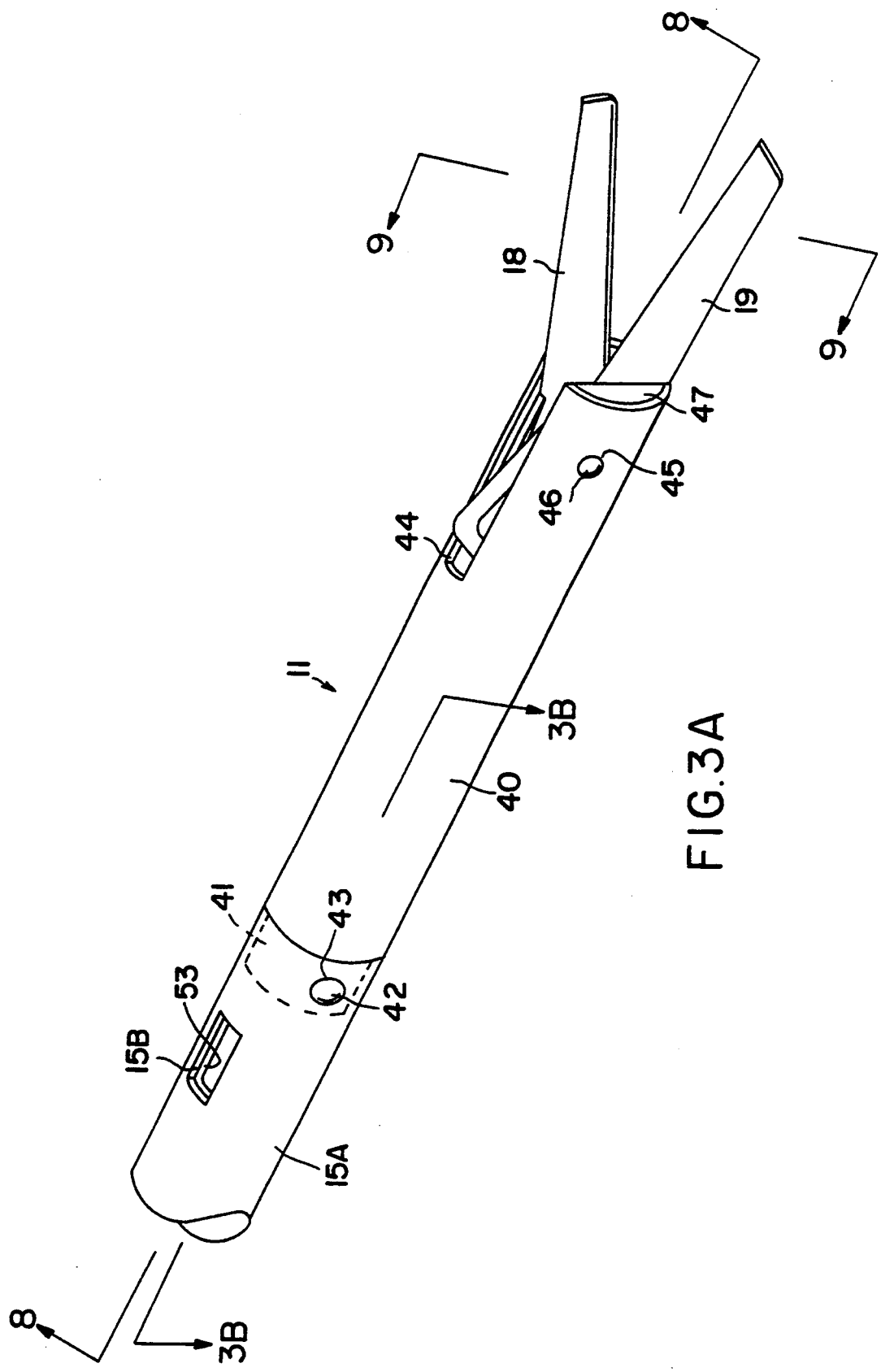
FIG. 3A is an elevation view of the distal end of instrument 10 taken along the line 3—3 of FIG. 1.
Figure 3B:
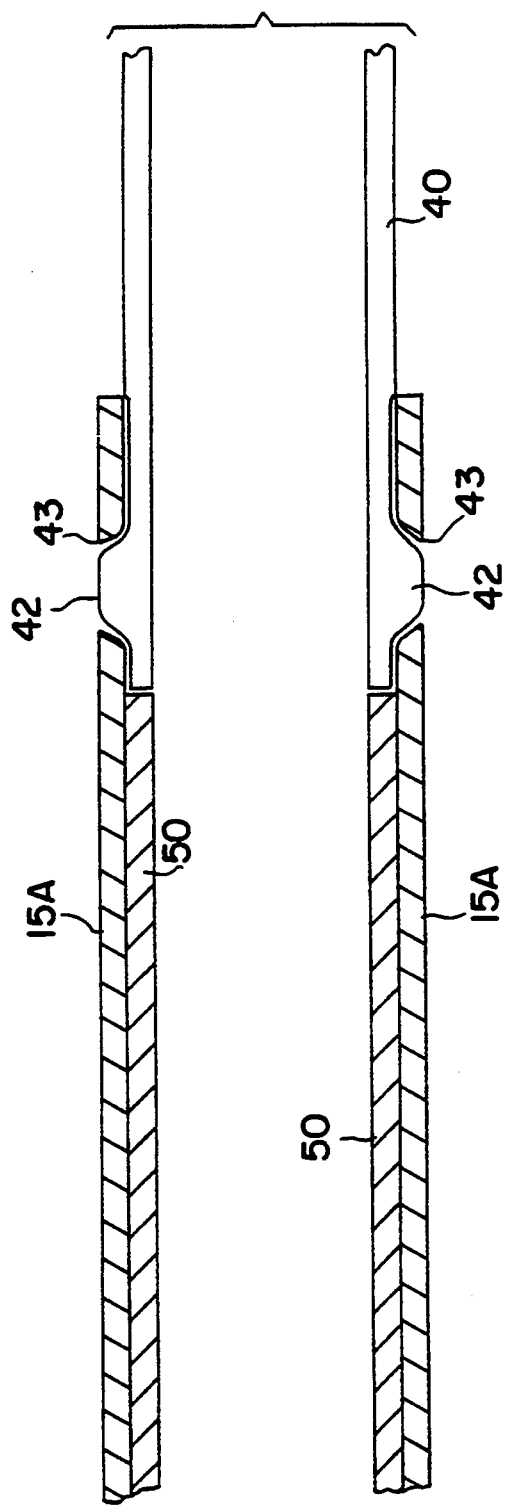
FIG. 3B is a cross-sectional plan view of the outer sleeve and distal end of the elongated barrel of instrument 10, taken along line 3B—3B of FIG. 3A.

Referring now to FIGS. 3A and 3B, a scissors-like embodiment of detachable working end 11 is described. Detachable working end 11 comprises outer sleeve 40 having a stepped proximal portion 41. Outer sleeve 40 has a length of about 7 cm compared to a length of about 33 cm for elongated barrel 15; both have outer diameters appropriate for use with conventional trocar tubes, i.e., about 5 mm. Protrusions 42 extend on either side of stepped portion 41 and engage apertures 43 in distal end 15A of elongated barrel 15. As shown in FIG. 3B, protrusions 42 have sloped edges where they contact apertures 43. Outer sleeve 40 of detachable working end 11 is friction fit into distal end 15A of elongated barrel 15 so that protrusions 42 hold outer sleeve 40 in position on elongated barrel 15 during the expected range of outward thrusts on working end 11 imposed by drive rod 16. Thus, outer sleeve 40 is held securely on distal end 15A of elongated barrel 15 during normal use, but may be detached from elongated barrel 15 by the application of sufficient force on detachable working end 11 while holding elongated barrel 15.

Also shown in FIG. 3A is access window 15B in distal end 15A of elongated barrel 15. Access window 15B provides access to window 53 of drive rod sleeve 50, as described hereinafter. Access window 15B and window 53 of drive rod sleeve 50 register only when drive rod 16 is at the distal-most limit of its stroke. The distal end of outer sleeve 40 includes diametrically opposed U-shaped slots 44 extending proximally from the distal end of outer sleeve 40. Apertures 45 in the distal end of outer sleeve 40 align across the diameter of the sleeve to accept insulating pivot pin 46.

Detachable working end 11 of instrument 10 includes first and second members 18 and 19.

Members 18 and 19 are configured to constitute the individual electrodes of a bipolar electrode instrument, as described in greater detail hereinafter. First and second members 18 and 19 comprise, for example, scissor halves pivotally connected by insulating pivot pin 46. Tube insulator halves 47 are disposed adjacent to the exterior surfaces of members 18 and 19 to electrically insulate those members from outer sleeve 40. Insulating pivot pin 46 has its ends flush with the outer surface of outer sleeve 40 and extends, from side to side, through a first tube insulator half 47, members 18 and 19, and a second tube insulator half 47.

Insulating pivot pin may comprise an electrically insulating metallic pin, e.g., anodized aluminum, having its ends deformed by peening. Alternatively, insulating pivot pin 46 may comprise a rod-like member having a threaded recess at either end to accept a screw. The screws engage the threaded recesses and permit an adjustable compressive load to be applied to outer sleeve 40, and hence members 18 and 19.

Figure 4:
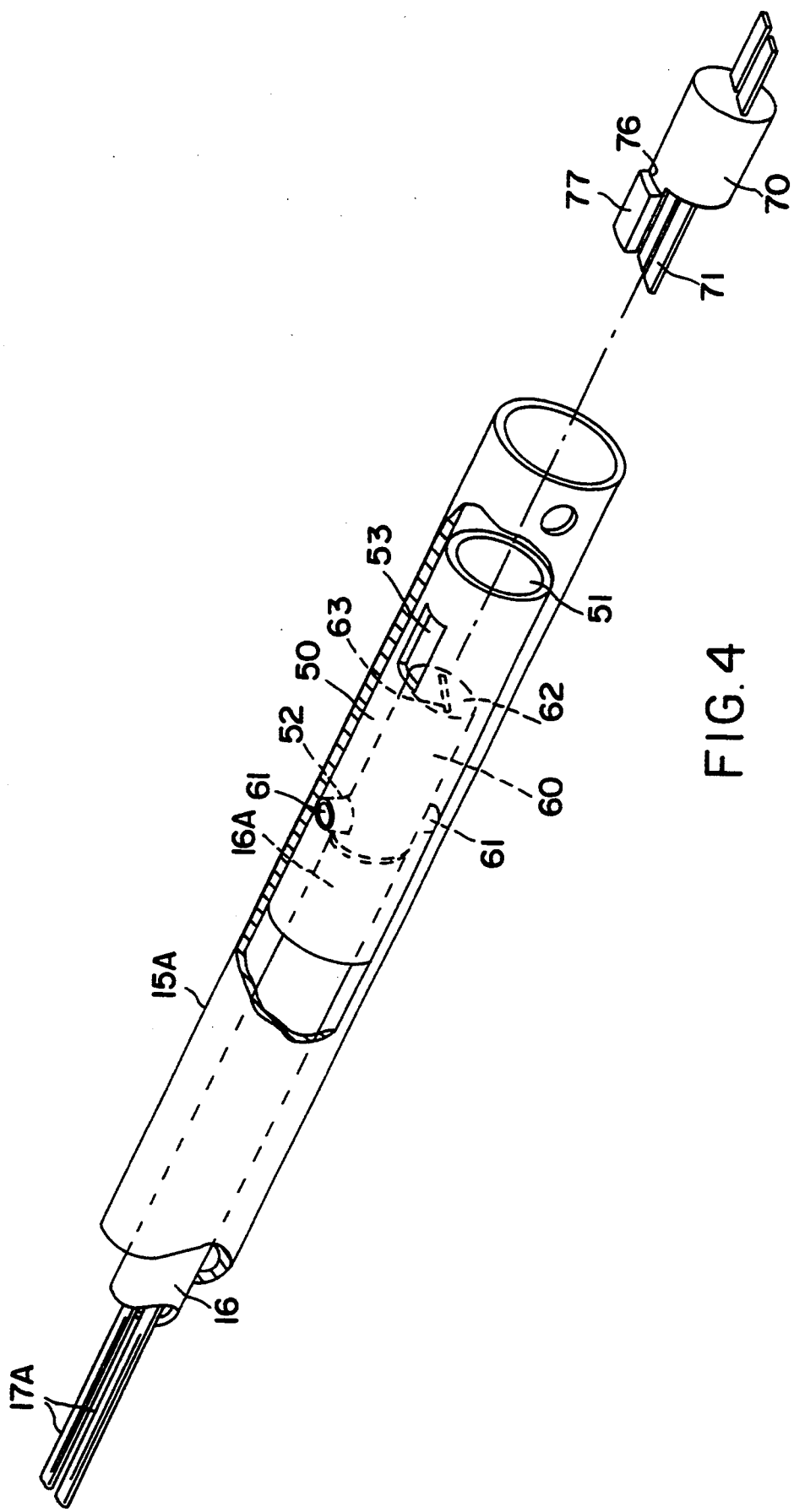
FIG. 4 is a perspective cut-away view similar to that of FIG. 3A showing the internal mechanism of the reusable handle of instrument 10.

Referring to FIG. 4, distal end 15A of the reusable handle portion of the present invention is described. As shown in FIG. 4, distal end 16A of drive rod 16 is coupled to drive rod sleeve 50 and electrical leads 17A connected to electrical terminals 17 pass through the central bore of drive rod 16. Drive rod sleeve 50 comprises a hollow sturdy sleeve, comprised of, for example, copper, having central bore 51 and diametrically opposed apertures 52. Drive rod sleeve 50 is bonded to distal end 16A of drive rod 16 using conventional bonding means such as glue, epoxy or a fastening pin (not shown). Drive rod sleeve 50 also includes window 53 for engaging latching tongue 76 and button 77 of detachable working end 11. As will be readily understood from FIG. 4, drive rod 16 and drive rod sleeve 50 coupled thereto reciprocate within the bore of elongated barrel 15 when handle members 12 and 13 are actuated.

Insulating block 60 is disposed within central bore 51 of drive rod sleeve 50. Insulating block 60 has upper and lower protrusions 61 that engage apertures 52 in drive rod sleeve 50, thereby fixing insulating block 60 within drive rod sleeve 50. Distal endface 62 of insulating block 60 includes slots 63 for accepting electrode strips 71 extending from the proximal endface of connector block 70 of working end 11.

Figure 6A:
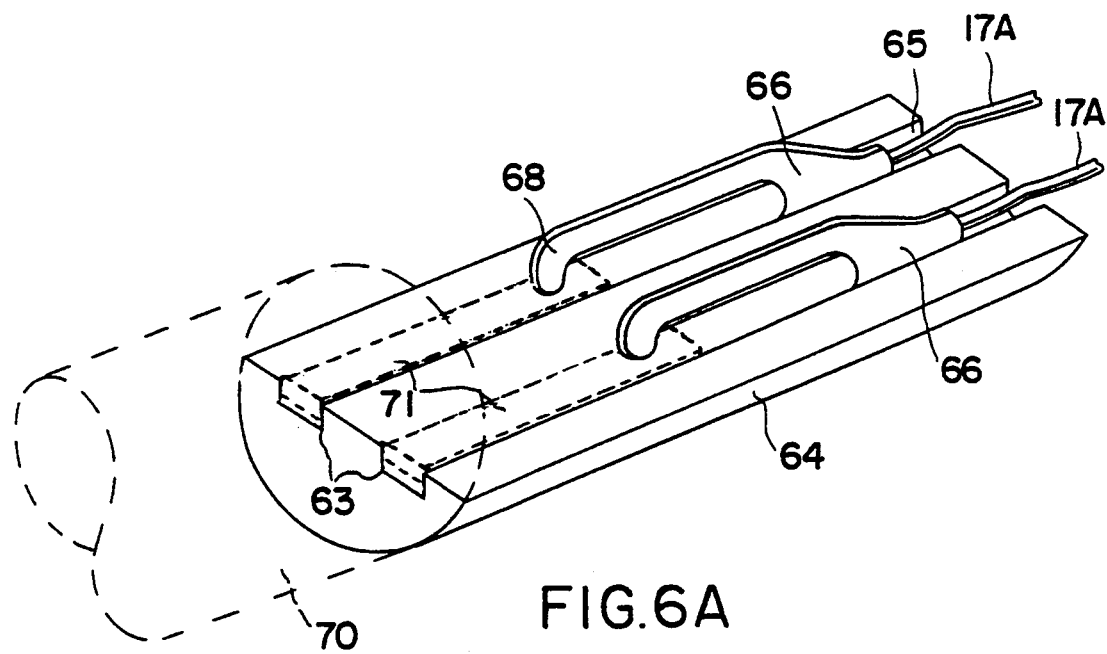
FIG. 6A is a partial perspective view of insulator block 50 of the present invention, showing engagement with phantom electrode strips 71.

As shown in FIGS. 5A, 5B and 6A, insulating block 60 may be formed of two injection molded halves 64. Insulating block 60 includes two parallel chambers 65 disposed perpendicularly to and communicating with slots 63. One electrical contact element 66 is disposed in each of chambers 65. Chambers 65 are dimensioned to engage the edges of electrical contact elements 66 securely and include widened portions 67 where they intersect slots 63 to enable fingers 68 and 69 to flex slightly to accept the electrode strips projecting from connector block 70, discussed hereinafter.

Electrical contact elements 66 are connected at the proximal end by conventional means, for example, by crimping or soldering, to electrical leads 17A. The distal ends of electrical contact elements 66 comprise fingers 68 and 69 that engage electrode strips 71 of connector block 70 of working end 11. Electrical contact elements 66 are comprised of a resilient alloy or metal, for example, a copper alloy containing 2% beryllium and 98% copper, and may be gold plated to facilitate a low impedance electrical connection with electrode strips 71 of working end 11.

Figure 6B:
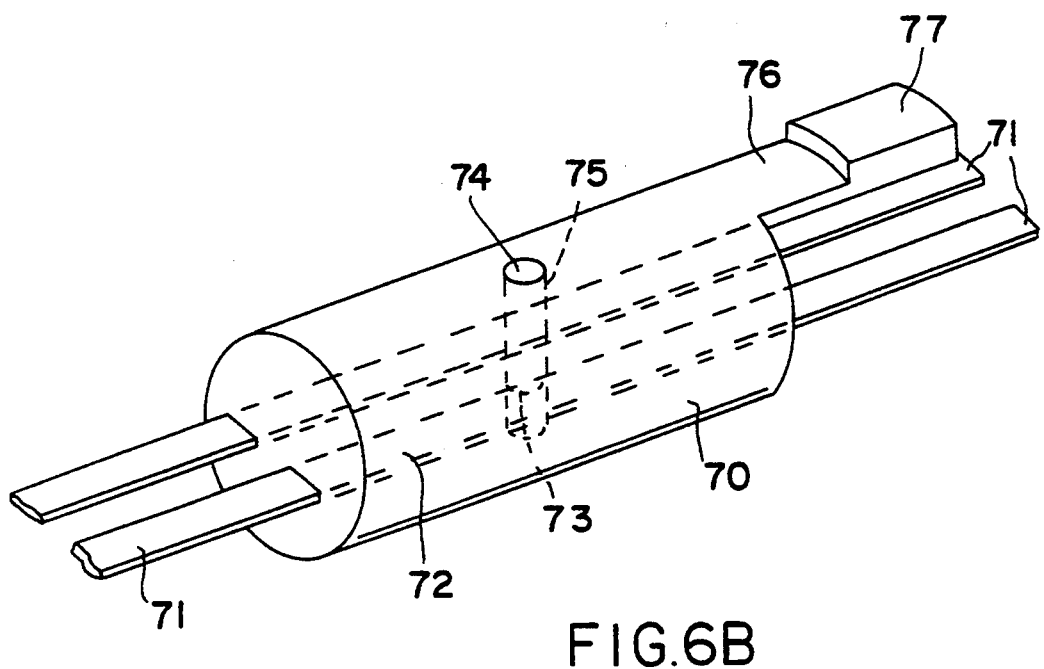
FIG. 6B is a perspective view of connector block 70 of the present invention.

Referring now to FIGS. 6A and 6B, insulator block 60 of the reusable handle portion is shown mated (in phantom lines) to connector block 70 of detachable working end 11. Connector block 70 is formed of sturdy electrically non-conducting material, for example, polyetherimide, and includes electrode strips 71 extending through passages 72 formed in connector block 70. Electrode strips 71 include a radiused indentation 73 that cooperates with plastic capture pin 74. Capture pin 74 is disposed in bore 75 that intersects passages 72, so that when capture pin 74 is inserted in bore 75, it engages the radiused indentations in electrode strips 71, thereby securing the electrode strips in position. Connector block 70 includes latching tongue 76 having raised button 77. Button 77 is dimensioned to interenegage with window 53 in drive rod sleeve 50 (see FIGS. 3A and 4), but does not extend into or engage with access window 15B in elongated barrel 15.

Button 77 is released from this engagement with window 53 of drive rod sleeve 50 by moving drive rod 16 to its distal-most limit, at which location window 53 registers with access window 15B in elongated barrel 15. When drive rod 16 is moved to this position (i.e., handle members 12 and 13 are spread apart) button 77 may be flexed inward by the user by depressing button 77 through access window 15B and window 53. By pulling on outer sleeve 40 while depressing button 77, working end 11 may be detached from the reusable handle portion of instrument 10.

Figure 7:
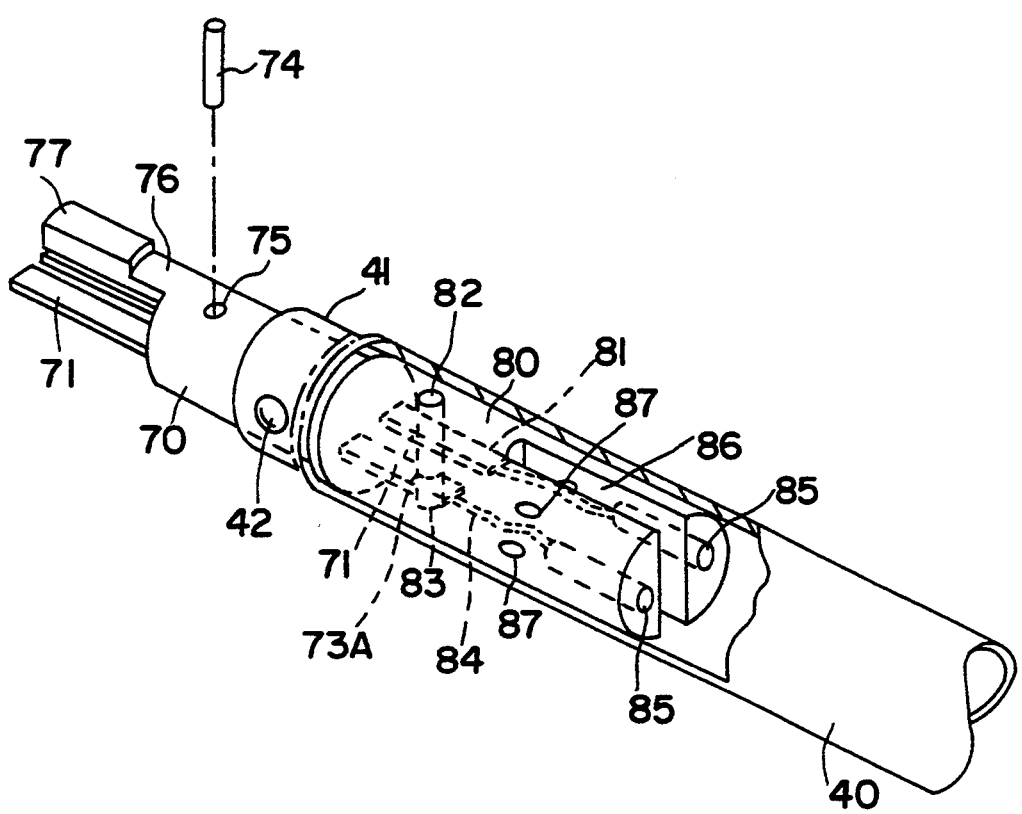
FIG. 7 is a perspective cut-away view similar to that of FIG. 3A showing the internal mechanism of working end 11 of the present invention.

As shown in FIG. 7, connector block 70 is slidably disposed within outer sleeve 40, where it is coupled to drive block 80. Connector block 70 and drive block 80 are disposed for reciprocation within outer sleeve 40. Drive block 80, like drive rod 16, may be formed of polyetherimide or polyaryletheretherkeytone, and includes slot-like passageways 81 to accept electrode strips 71 extending from connector block 70. Electrode strips include a second radiused indentation 73A so that second capture pin 82 disposed in bore 83 secures electrode strips in position, as described above with respect to capture pin 74. Electrode strips 71 have leads 84 soldered to their distal ends that are in turn connected to receptacles 85. Receptacles 85 electrically couple electrode assembly 90, to be described hereinafter, to the power supply via terminals 17, leads 17A and electrode strips 71. Drive block 80 also includes yoke 86, and transverse bores 87, for engaging electrode assembly 90, as described hereinafter.

Figure 8:
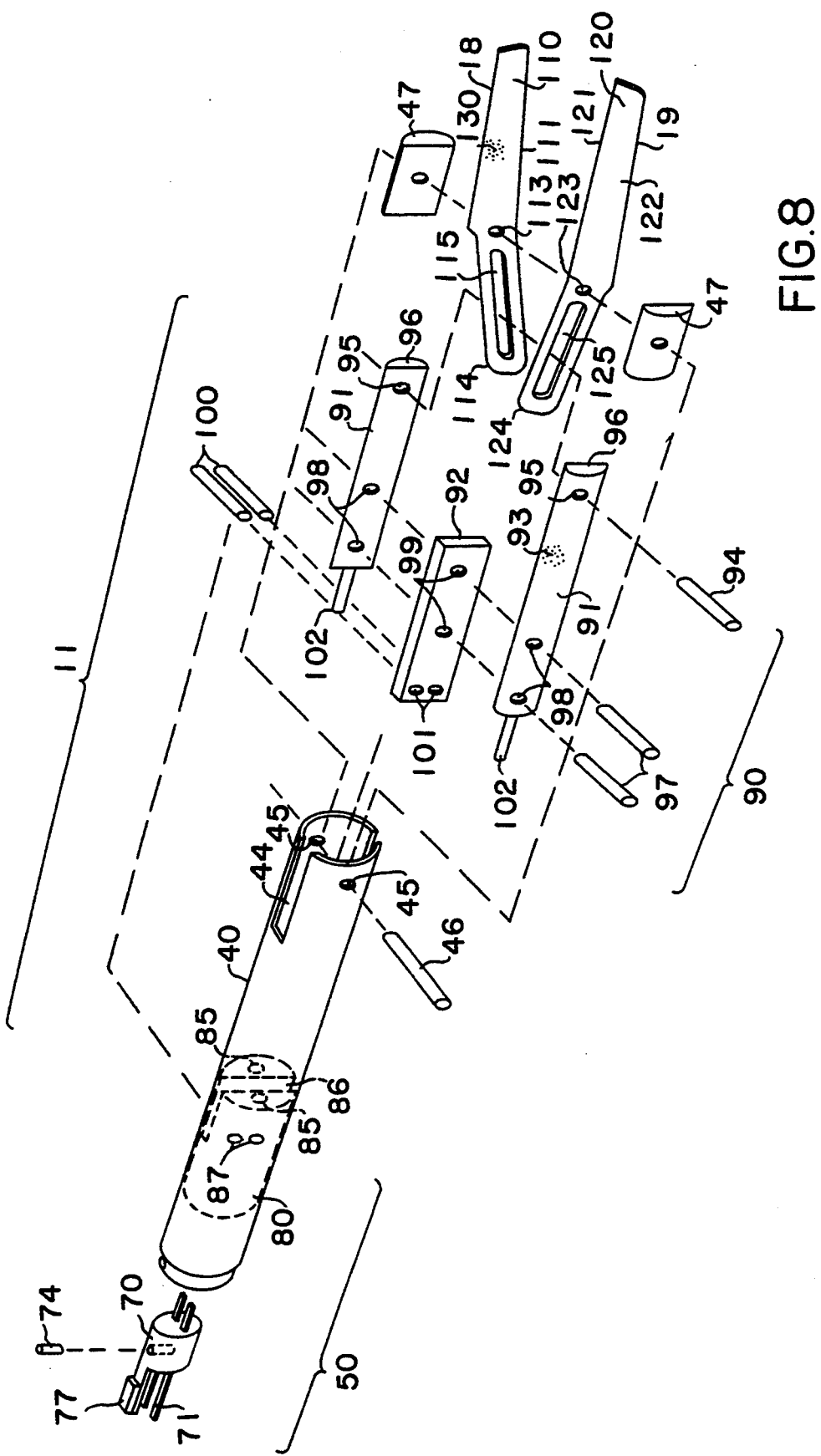
FIG. 8 is an exploded perspective view of the working end of the instrument taken along line 8—8 of FIG. 3A.

Referring now to FIG. 8, electrode assembly 90 comprises semi-circular electrode halves 91 separated by insulating strip 92. Insulating strip 92 extends from the distal end of drive block 80 to a position near the shanks of the movable members to form a slot for accepting the shanks of the movable members 18 and 19. The inner surfaces of electrode halves 91 should not include a layer of insulating material, because insulating strip 92 serves to electrically isolate the electrode halves from each other and the inner surfaces of electrode halves 91 must make sliding electrical contact with shanks 114 and 124 of movable members 18 and 19.

The outer surfaces of electrode halves 91 are coated with an abrasion-resistant electrically insulating material 93 that electrically isolates the electrode halves from outer sleeve 40. Insulating material 93 may comprise, for example, glass, ceramic, Teflon or polyetherimide. Insulating drive pin 94 extends through apertures 95 located near the distal endfaces of the electrode halves.

Still referring to FIG. 8, electrode halves 91 are affixed to either side of insulating strip 92 by insulating pins 97. Insulating pins 97 extend through apertures 98 in electrode halves 91 and apertures 99 in insulating strip 92, respectively. Insulating pins may comprise a sturdy electrically insulating material, for example, ceramic or anodized aluminum.

The proximal end of insulating strip 92 is inserted into slot 86 in the distal end of drive block 80, and is affixed to the distal end of drive block 80 by pins 100. Pins 100 extend through apertures 87, provided for that purpose adjacent slot 86 in drive block 80, and apertures 101 in insulating strip 92, respectively. Pins 100 may comprise a sturdy electrically conducting or insulating material, inasmuch as pins 100 do not form a part of the electrical circuit of instrument 10. Thus, pins 100 may comprise, for example, either stainless steel or alumina. Electrode halves 91 are electrically connected to receptacles 85 via electrical connectors 102 projecting from the proximal endfaces of electrode halves 91, or may be soldered using lead wires to connect electrode halves 91 to electrode strips 71.

As shown in FIGS. 8 and 9A–C, members 18 and 19 include, respectively, shearing surfaces 110 and 120, cutting edges 111 and 121, exterior surfaces 112 and 122, apertures 113 and 123, and shank portions 114 and 124. A thin layer 130 of insulating coating is provided on one (FIG. 6B) or both (FIG. 6A) of the opposing mating surfaces of members 18 and 19, including one or both of the shearing surfaces 110 and 120, and one or both of the mating surfaces of the shank portions 114 and 124.

Members 18 and 19 are configured to constitute the individual electrodes of a bipolar electrode instrument. In a first family of embodiments, illustrated in FIGS. 6A and 6B, opposing members 18 and 19 are made of an electrically conducting material and serve as both the electrodes and shearing surfaces. In a second family of embodiments, illustrated in FIG. 6C, the opposing members are made of an electrically insulating material and have electrically conductive portions disposed on the exterior surfaces. In FIGS. 6A through 6C, members 18 and 19 are shown in contact with tissue 200.

For the scissors-like embodiment of the working end shown in FIGS. 1–8, members 18 and 19 may be constructed of metallic alloys that offer good electrical conduction, adequate hardness and tensile strength sufficient to allow the members to be oriented toward each other to effect adequate wiping at the cutting edges. Materials having these characteristics include stainless steel, e.g., 301, 302, 304 and 316, martensitic stainless steels, e.g. 410, 420, 430 and 440, and precipitation hardened steels, e.g., 17-4PH and 17-7PH alloys. The use of such materials permit members 18 and 19 to be formed by numerous methods, including forging followed by machining, die casting, metal injection molding, and electrodischarge machining (EDM) cut-out of the features.

Exterior surfaces 112 and 122 of the members may have optional coating 131 of a high electrical and thermal conductivity material, e.g., silver or copper, other than on their respective shearing surfaces 110 and 120. Coating 131 facilitates good electrical contact between exterior surfaces 112 and 122 and the tissue that comes into contact with those surfaces as members 18 and 19 are moved relative to one another.

Coating 131 reduces localized heating of the exterior surfaces 112 and 122 of members 18 and 19 by dissipating the heat throughout the thermally conducting surface area of the coating. Coating 131 also reduces the likelihood that joulean heating of members 18 and 19 will occur, because any localized current flow is re-distributed throughout the entire coating. Consequently, coating 131, if applied, reduces thermal decomposition and sticking of blood and tissue to exterior surfaces 112 and 122 during use.

Layer 130 of insulating coating covers the inside face of one or both of cutting edges 111 and 121, so that the cutting edges are electrically isolated from each other. Thus, current flows through tissue 200 between exterior surfaces 112 and 122 of members 18 and 19 in the region near cutting edges 111 and 121, while ensuring that members 18 and 19 do not electrically contact each other within the range of the cutting or opening motion of the members.

Consequently, hemostasis of tissue occurs at a location just in advance of the cutting point while cutting edges 111 and 121 simultaneously sever the hemostatically heated tissue. This configuration enables the cutting edges to contact each other to sever tissue while preventing short circuiting, which would impede simultaneous coagulation of the blood vessels extending through the tissue. Layer 130 substantially prevents current flow directly between opposing shearing surfaces 110 and 120 when members 18 and 19 are closed together. Rather, the current flows through the path of least resistance between the electrodes, i.e., through the tissue in direct contact with regions 132 and 133, respectively, of exterior surfaces 112 and 122 of the members. This current flow is represented schematically by flux lines 201 shown in FIGS. 6A–6C.

The arrangement of the present invention confines current flow between regions 132 and 133 of exterior surfaces 112 and 122 to a region from where cutting edges 111 and 121 contact each other to a point distal to the cutting point. That distal point is where either the tissue no longer forms an electrical connection between the electrode surfaces or the spacing between members 18 and 19 is sufficiently large that the current density is too low to cause significant joulean heating of the tissue.

It is therefore apparent that as members 18 and 19 gradually close together, the cutting point moves along cutting edges 111 and 121 distally of insulating pivot pin 46 and is preceded by a region in which a current flows from one member to the other to achieve hemostasis of the tissue. Thus, hemostasis occurs at a location just in advance of the cutting point while cutting edges 111 and 121 simultaneously sever the hemostatically heated tissue.

Because shank portions 114 and 124 also move through a range of motion wherein the opposing mating surfaces of shank portions 114 and 124 move across each other, layer 130 disposed on one or both of the opposing mating surfaces of the shank portions prevents electrical shorting between those surfaces as well. Thus, layer 130 electrically isolates shank portions 114 and 124 in the same manner that it electrically isolates shearing surfaces 110 and 120. Alternatively, layer 130 need not be disposed on the interior surfaces of one or both shank portions 114 and 124, but may comprise an electrically insulating washer disposed, for example, on insulating drive pin 94 between shank portions 114 and 124, thereby separating the shank portions.

Referring again to FIG. 8, shank portions 114 and 124 of members 18 and 19 include angled slots 115 and 125. The exterior surfaces of shank portions 114 and 124 contact the interior surfaces of electrode halves 91 within the slot formed by electrode halves 91 and insulating strip 92. Since the interior surfaces of electrode halves 91 are not covered by insulating material 93, electrode halves 91 are in direct electrical contact with shank portions 114 and 124.

Members 18 and 19 and electrode halves 91 are constructed of a metallic material that provides good electrical contact, such that the sliding contact resistance of each member 18 and 19 and its respective electrode halve 91 is less than 5 ohms, and preferably less than 1 ohm. The interior surfaces of electrode halves 91 and the exterior surfaces of shank portions 114 and 124 may be gold plated to reduce the sliding electrical contact resistance.

Accordingly, the electrical circuit energizing each bipolar electrode extends from electrical terminals 17 on the proximal portion 30 of drive rod 16, through lead 17A, electrode strip 71, and lead 84 to electrode halve 91. The outwardly disposed shank portion of the respective members 18 and 19 are in sliding electrical contact with the interior surfaces of electrode halves 91, thereby providing a voltage potential across the tissue contacting portions of working end 11. Insulating strip 93 electrically isolates electrode halves 91, while layer 130 of insulating material on one or both of members 18 and 19 electrically isolates those members, as described heretofore.

Insulating drive pin 94 extends through slots 115 and 125 of shank portions 114 and 124. The ends of insulating drive pin 94 are disposed in apertures 95 of electrode halves 91 so that they do not interfere with reciprocatory movement of electrode assembly 90 and its associated drive members in outer sleeve 40. Insulating pin 94 may be comprised of, for example, silicon nitride, zirconia, alumina, or other material which has the mechanical strength to withstand the loads imposed on the pins during opening and closing of members 18 and 19, while providing the requisite electrical insulation between shank portions 114 and 124.

As shown in FIGS. 10A and 10B, slots 115 and 125 are configured so that when the handle members are actuated to urge drive rod 16 in a distal direction, insulating drive pin 94 is urged to the distal ends of slots 115 and 125, thereby opening members 18 and 19 (see FIG. 10A). In this first position, working end 11 may be positioned so that members 18 and 19 are located proximate to the tissue, without imposing any mechanical load thereon.

On the other hand, when handle members 12 and 13 are rotated away from each other, drive rod 16 is reciprocated proximally. This motion pulls drive pin 94 toward to the proximal ends of slots 115 and 125, thereby closing members 18 and 19 as shown in FIG. 10B. As members 18 and 19 are gradually closed, the cutting point defined by the intersection of cutting edges 111 and 121, moves along those cutting edges, so that a current flows through the tissue to cause hemostasis of the tissue immediately prior to its being severed mechanically. Thus, in this second position, hemostasis is achieved in the tissue by the current flowing between members 18 and 19, and then mechanically severed.

Layer 130 of electrically insulating material may have a hardness that is greater or substantially greater than the steel or other electrically conducting material used to manufacture conventional scissors-like devices. For example, members 18 and 19 may be made of a martensitic stainless steel, e.g., AISI 420. Insulating layer 130 may then comprise, for example, a ceramic material such as alumina or zirconia, or an inorganic electrically insulating material such as a glass, nitride, boride or synthetic diamond. Depending upon the material selected, layer 130 may be deposited on shearing surface 112 of member 18 by conventional techniques, for example, plasma or flame-sprayed deposition. The applied coating forms a non-conductive cutting edge for that member and has a greater hardness than the steel substrate and the steel of opposing member 19. Consequently, as layer 130 rubs against the cutting edge 121 or shearing surface 120 of member 19, steel shearing surface 120 and cutting edge 121 are mechanically ground or polished by the harder insulating layer 130. Cutting edges 111 and 121 are therefore self-sharpening and remain sharp during continued use.

Insulating layer 130 has a thickness in the range of 0.002 inches to about 0.050 inches, more preferably 0.003 to 0.007 inches. The applicant has determined that at thicknesses 0.001 inch or less, the thickness of the insulating layer 130 is insufficient to prevent shorting of the electrodes. Insulating layer thicknesses above 0.002 inches and below 0.050 inches cause adequate hemostasis. It has been observed, however, that the greater the minimum distance between the proximate current conducting portions of the opposing electrodes in the region of current flow through the tissue, the longer the current path through the tissue and the more difficult it becomes to obtain the desired localized and intense heating to achieve adequate hemostasis. Insulating layer thicknesses above 0.050 inches are believed to be too large for most practical applications, for the ceramic insulating materials described.

Figure 9A:
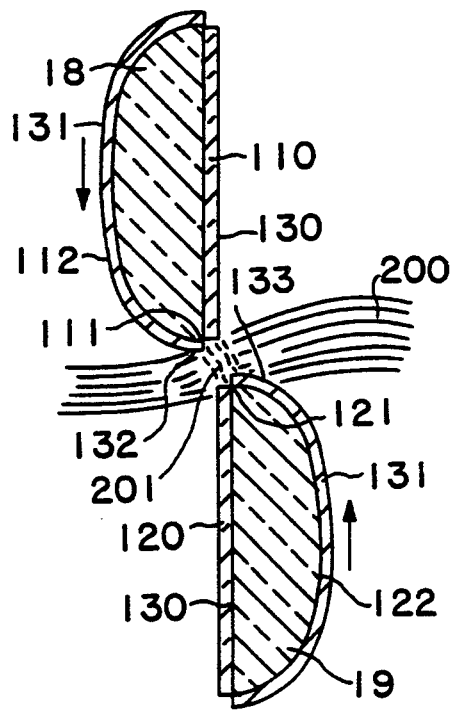
FIGS. 9A, 9B, and 9C show, respectively, cross-sections of alternative embodiments of the detachable working end of the instrument shown in FIG. 3A, taken along line 9—9 of FIG. 3A.
Figure 9B:
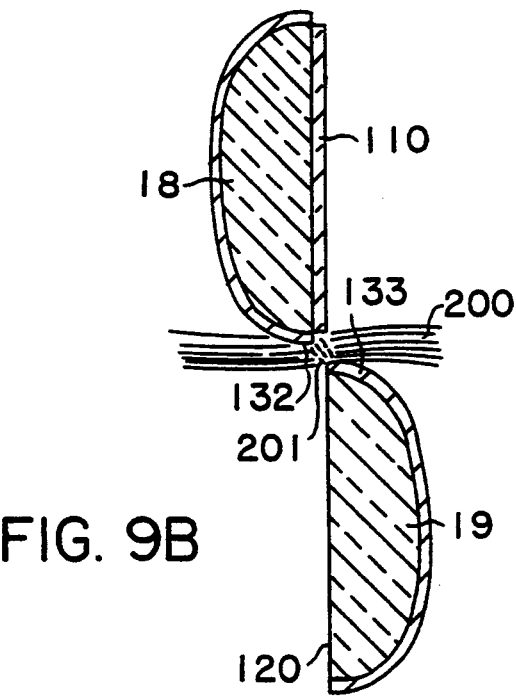
Figure 9C:
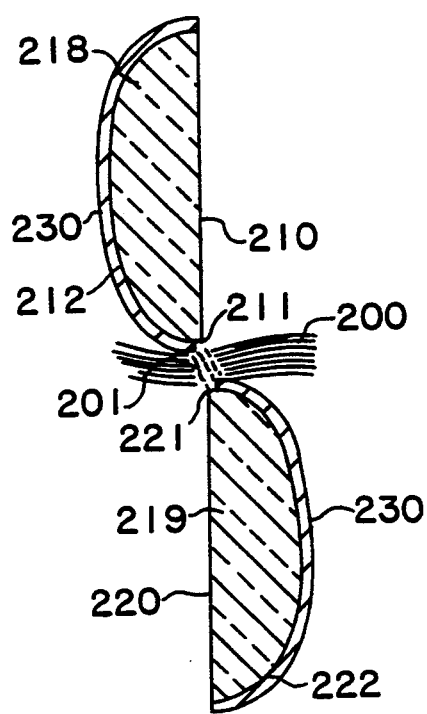

Referring to FIG. 9C, an embodiment representative of a second family of embodiments constructed in accordance with the present invention is described, with similar components indicated by numbers increased by 100. In this embodiment, which outwardly resembles the instrument of FIG. 10A, opposing members 218 and 219 are made of an electrically insulating material, e.g., a ceramic material such as zirconium oxide or aluminum oxide-based ceramics. The exterior surfaces 212 and 222 of members 118 and 119, i.e., those portions other than the shearing surfaces 210 and 220 and cutting edges 211 and 221, have coating 230 comprising a material of high electrical and thermal conductivity, e.g., copper, silver or nickel. Coating 230 thereby provides opposing electrodes for conduction of high frequency current through tissue between coatings 230 on exterior surfaces 212 and 222 of members 118 and 119. In this embodiment, coating 230 covers most of the exterior surface of shearing members 118 and 119 such that the current carrying sections closest to cutting edges 211 and 221 are no closer than 0.002 to 0.050 inches, and more preferably 0.003 to 0.007 inches. With the configuration of the embodiment of FIG. 9C, members 118 and 119 provide the desired insulating material between the electrodes.

Referring now to FIGS. 11A and 11B, an alternate embodiment of working end 11 of the present invention is described, in which like-primed numbers designate similar elements. Jaw-like members 18' and 19' have shank portions 114' and 124' respectively. Shank portions 114' and 124' in turn have angled slots 115' and 125' respectively Insulated drive pin 94' extends through slots 115' and 125' and has its ends secured in apertures 95' of electrode halves 91'. Members 18' and 19' have grasping surfaces 110' and 120', teeth 111' and 121', and exterior surfaces 112' and 122' respectively Teeth 111' and 121' are disposed in opposing relation on grasping surfaces 110' and 120' to grasp tissue captured between members 18' and 19'. Alternatively, the grasping surfaces may include a pattern of pyramidal teeth that serve to grasp the tissue.

As for the embodiment of FIGS. 10A and 10B, members 18' and 19' of the device of FIGS. 11A-B comprise the electrodes of a bipolar device. A thin layer 130' of insulation may be disposed on one or both of the mating surfaces of shank portions 114' and 124' to prevent electrical shorting between members 18' and 19' when those members are moved between the open and closed positions. Alternatively, layer 130' may comprise an insulating washer disposed on insulating drive pin 94' between the shank portions to electrically isolate shank portions 114' and 124'.

Layer 130' of insulating material may in addition cover the opposing surfaces of teeth 111' and 121' of the respective members. Alternatively, teeth 111' and 121' may be dimensioned so that when the members are in the closed position, a gap exists between teeth 111' and 121' sufficient to prevent direct shorting between the members.

Actuation of the handle members of the instrument urges drive pin 94' to move members 18' and 19' from a first position where the members can be disposed around a mass of tissue, to a second position where the members grasp the tissue. Members 18' and 19' therefore move through a graspers-like range of motion, similar to that of a conventional pliers. In the second position, current flows between members 18' and 19' to achieve hemostasis of the tissue captured therebetween.

Exterior surfaces 112' and 122' of members 18' and 19' may have a smooth, rounded, cross-section to facilitate blunt dissection. For example, such an instrument may be inserted—with members 18' and 19' closed together—into an incision made in a multilayer tissue mass. In this first position, the tissue merely contacts the outer surface of members 18' and 19', without imposing a substantial mechanical load thereon.

The electrodes may then be energized, and jaw-like members 18' and 19' may be gradually opened to separate the layers of tissue while simultaneously causing hemostasis of the tissue. When members 18' and 19' are moved to this second position, the outer surfaces of the members engage the tissue and separate the tissue layers along tissue boundaries without severing.

In addition, members 18 and 19 of working end 11 of the present invention may be configured as shown in my copending U.S. patent application Ser. No. 07/877,704 now U.S. Pat. No. 5,330,471. Thus, for example, the tips of members 18 and 19 may be curved so that they lie in a plane parallel to the longitudinal axis of instrument 10. Because the endoscope is typically inserted into the surgical area adjacent to the surgical instrument, the parallax resulting from the acute angle formed between the endoscope and the surgical instrument may restrict the surgeon's view of the surgical site. Thus, the surgeon may have only a limited view of the working end of the surgical instrument.

Providing a curved working end, so that its tips lie in a plane parallel to the longitudinal axis of elongated barrel 15, resolves this difficulty and enhances the surgeon's view of the working end, thereby enhancing the precision of the surgical procedure. To ensure that the working end of the instrument will pass easily through standard trocar tubes, the tips of members 18 and 19 should not extend beyond the diameter of elongated barrel 15.

The various embodiments described herein are presented for purposes of illustration and not limitation, as the present invention can be practiced with endoscopic surgical instruments of any type having two opposing members movable with respect to one another. The instruments and methods of the present invention may be adapted, as may be required, for use in operating on any internal tissue, vessel, or organ.

For example, the present invention may be practiced using an actuating means comprising a pistol style grip having a spring-biased trigger to reciprocate drive rod 16, rather than the handle members described hereinbefore. One skilled in the art will appreciate that the present invention can be practiced by other than the described embodiments, and that the present invention is limited only by the claims that follow.

What is claimed is:

1. A detachable working end for use in endoscopic electrosurgery, the detachable working end adapted to be connected to an end of a reusable handle portion having an elongated barrel, the detachable working end adapted to be actuated by a drive rod reciprocated through the elongated barrel, the drive rod providing first and second electrical contacts, the working end comprising:

an outer sleeve adapted to be engaged in fixed relation to the elongated barrel;

a connector block slidably disposed within the outer sleeve and adapted for coupling to the drive rod for translational movement relative to the outer sleeve, the connector block having a proximal end including means for mating with the first and second electrical contacts and a distal end including first and second legs;

a pivot pin having first and second ends mounted in the outer sleeve;

first and second members disposed on the pivot pin for relative rotation from a first position to a second position, the first and second members having shank portions defining longitudinally directed slots, the shank portions of the first and second members electrically coupled to the means for mating with the first and second electrical contacts; and a drive pin mounted between the first and second legs and disposed through the longitudinally directed slots of the first and second members, so that the first and second members are movable responsive to reciprocation of the drive rod and the first and second members provide first and second electrodes for passing current through tissue to cause hemostasis thereof.

2. A detachable working end as defined in claim 1 wherein the outer sleeve has a longitudinal axis, the first and second members have first and second tips, and the first and second members are curved so that the first and second tips lie in a plane parallel to and separated from the longitudinal axis of the outer sleeve.

3. A detachable working end as defined in claim 1 wherein the first and second members have opposing mating surfaces, the detachable working end further comprising electrically insulative material interposed between the opposing mating surfaces of the first and second members.

4. A detachable working end as defined in claim 3 wherein the first member comprises a first grasping surface and the second member comprises a second grasping surface, the detachable working end further comprising:

means for connecting the first and second members so that the first and second grasping surfaces move through a range of motion in a graspers-like action to grasp tissue disposed therebetween, and the electrically insulating material is interposed between the first and second electrodes so that current passes between the first and second electrodes and through the tissue disposed between the first and second grasping surfaces.

5. A detachable working end as defined in claim 4 wherein the first and second members are made of an electrically conductive material.

6. A detachable working end as defined in claim 5 wherein portions of the first and second grasping surfaces define serrations or a pyramidal array for grasping the tissue.

7. A detachable working end as defined in claim 3 wherein the first member comprises a first shearing surface, a first cutting edge, and a first exterior surface and the second member comprises a second shearing surface, a second cutting edge, and a second exterior surface, the detachable working end further comprising:

means for connecting the first and second members so that the first shearing surface moves relative to the second shearing surface through a range of motion in a scissors-like cutting action, wherein the first and second cutting edges close together for shearing tissue located therebetween, the scissor-like cutting action defining a cutting point located just distally of where the first and second cutting edges come together, the cutting point moving distally along the cutting edges where the first and second cutting edges come together through the range of motion, the first and second electrodes moving through the same range of motion as the first and second shearing surfaces, and the electrically insulative material is interposed between the first and second electrodes so that current passes between the first and second electrodes distal to the cutting point and not between the first and second shearing surfaces.

8. A detachable working end as defined in claim 7 wherein the first and second members are made of an electrically conductive material, and the electrically insulative material is a first layer of material disposed on the first shearing surface to form the first cutting edge and the first shearing surface.

9. An instrument as defined in claim 8 wherein the first layer has a thickness selected in a range of 0.002 to 0.050 inches.

10. A detachable working end as defined in claim 8 further comprising a second layer of electrically insulative material disposed on the shearing surface of the second member to form the second cutting edge and the second shearing surface.

11. A detachable working end as defined in claim 10 wherein the first layer has a first thickness and the second layer has a second thickness and the sum of the first and second thicknesses is in a range of 0.002 and 0.050 inches.

12. An instrument for performing endoscopic electrosurgery on a tissue by passing current through the tissue to cause hemostasis thereof, the instrument comprising:

a reusable handle portion comprising:

an elongated barrel having a proximal end, a distal end and a central bore;

engagement means disposed at the distal end of the elongated barrel for removably engaging a detachable working end;

a drive rod slidably disposed in the central bore for reciprocation in the proximal and distal directions, the drive rod providing first and second electrical contacts, actuating means connected to the proximal end of the elongated barrel for causing reciprocation of the drive rod; and a detachable working end comprising:

an outer sleeve adapted to be engaged to the engagement means;

a connector block slidably disposed within the outer sleeve and adapted for coupling to the drive rod for translational movement relative to the outer sleeve, the connector block including a proximal end having means for mating with the first and second electrical contacts and a distal end including first and second legs;

a pivot pin having first and second ends mounted in the outer sleeve;

first and second members disposed on the pivot pin for relative rotation from a first position to a second position, the first and second members having shank portions defining longitudinally directed slots, the shank portions of the first and second members electrically coupled to the means for mating with the first and second electrical contacts; and a drive pin mounted between the first and second legs and disposed through the longitudinally directed slots of the first and second members, so that the first and second members are movable responsive to reciprocation of the drive rod and the first and second members provide first and second electrodes.

13. An instrument as defined in claim 12 wherein the actuating means comprises first and second handle members and means for fastening the first and second handle members together for relative movement.

14. An instrument as defined in claim 12 wherein the outer sleeve has a longitudinal axis, the first and second members have first and second tips, and the first and second members are curved so that the first and second tips lie in a plane parallel to and separated from the longitudinal axis of the outer sleeve.

15. An instrument as defined in claim 12 wherein the first and second members are made of an electrically conductive material.

16. An instrument as defined in claim 15 wherein portions of the first and second grasping surfaces define serrations or a pyramidal array for grasping the tissue.

17. An instrument as defined in claim 12 wherein the first and second members have opposing mating surfaces, the detachable working end further comprising electrically insulative material interposed between the opposing mating surfaces of the first and second members.

18. An instrument as defined in claim 17 wherein the first member comprises a first grasping surface and the second member comprises a second grasping surface, the detachable working end further comprising:
  means for connecting the first and second members so that the first and second grasping surfaces move through a range of motion in a graspers-like action to grasp tissue disposed therebetween and the electrically insulating material is interposed between the first and second electrodes current passes between the first and second electrodes and through the tissue disposed between the first and second grasping surfaces.

19. An instrument as defined in claim 17 wherein the first member comprises a first shearing surface, a first cutting edge, and a first exterior surface and the second member comprises a second shearing surface, a second cutting edge, and a second exterior surface, the detachable working end further comprising:
  means for connecting the first and second members so that the first shearing surface moves relative to the second shearing surface through a range of motion in a scissors-like cutting action, wherein the first and second cutting edges close together for shearing tissue located therebetween, the scissor-like cutting action defining a cutting point located just distally of where the first and second cutting edges come together, the cutting point moving distally along the cutting edges where the first and second cutting edges come together through the range of motion, the first and second electrodes moving through the same range of motion as the first and second shearing surfaces, and the electrically insulative material is interposed between the first and second electrodes so that current passes between the first and second electrodes distal to the cutting point and not between the first and second shearing surfaces.

20. An instrument as defined in claim 19 wherein the first and second members are made of an electrically conductive material and the electrically insulative material is a first layer of material disposed on the first shearing surface to form the first cutting edge and the first shearing surface.

21. An instrument as defined in claim 20 wherein the first layer has a thickness selected in a range of 0.002 to 0.050 inches.

22. An instrument as defined in claim 20 further comprising a second layer of electrically insulative material disposed on the shearing surface of the second member to form the second cutting edge and the second shearing surface.

23. An instrument as defined in claim 22 wherein the first layer has a first thickness and the second layer has a second thickness and the sum of the first and second thicknesses is in a range of 0.002 and 0.050 inches.

24. A detachable working end for use in endoscopic electrosurgery, the detachable working end adapted to be connected to an end of a reusable handle portion having an elongated barrel, the detachable working end adapted to be actuated by a drive rod reciprocated through the elongated barrel, the drive rod providing first and second electrical contacts, the working end comprising:
  an outer sleeve;
  first and second shearing members disposed in said outer sleeve and movable with respect to each other responsive to reciprocation of the drive rod, the first shearing member having a first shearing surface, a first cutting edge having a length, and a first exterior surface, a portion of the first exterior surface adjacent the first cutting edge defining a first electrode;
  the second member having a second shearing surface, a second cutting edge, and a second exterior surface, a portion of the second shearing member adjacent the second cutting edge defining a second electrode;
  means for connecting the first and second members so that the first shearing surface moves relative to the second shearing surface through a range of motion in a scissors-like cutting action, wherein the first and second cutting edges close together for shearing tissue located therebetween, the scissor-like cutting action defining a cutting point located just distally of where the first and second cutting edges come together, the cutting point moving distally along the cutting edges where the first and second cutting edges come together through the range of motion;
  an electrically insulative material interposed between the first and second electrodes so that the first and second electrodes do not contact each other in the range of motion and so that the current passes between the first and second electrodes distal to the cutting point and not between the first and second shearing surfaces, the first and second cutting edges cutting the tissue at the cutting point;
  means for removably securing the outer sleeve to the elongated barrel to prevent relative motion therebetween;
  drive means for coupling the first and second shearing members to the drive rod;
  means for removably engaging the drive means to the drive rod; and
  means for coupling each of the first and second electrodes to a respective one of the first and second electrical contacts,
  wherein the first and second shearing members comprise an electrically conductive material, the means for connecting the first and second shearing members comprises a material that does not conduct electricity and the electrically insulative material comprises a first layer of material disposed on the first shearing surface to form substantially the entire length of the first cutting edge and the first shearing surface.

25. An instrument as defined in claim 24 wherein the first layer has a thickness selected in a range of 0.002 to 0.050 inches.

26. A detachable working end as defined in claim 24 further comprising a second layer of electrically insulative material disposed on the shearing surface of the second member to form the second cutting edge and the second shearing surface.

27. A detachable working end as defined in claim 26 wherein the first layer has a first thickness and the second layer has a second thickness and the sum of the first and second thicknesses is in a range of 0.002 and 0.050 inches.

28. An instrument for performing endoscopic electrosurgery on a tissue by passing current through the tissue to cause hemostasis thereof, the instrument comprising:
   a reusable handle portion comprising:
      an elongated barrel having a proximal end, a distal end and a central bore;
      a drive rod slidably disposed in the central bore for reciprocation in the proximal and distal directions, the drive rod providing first and second electrical contacts,
      actuating means connected to the proximal end of the elongated barrel for causing reciprocation of the drive rod; and
   a detachable working end comprising:
      an outer sleeve;
      first and second shearing members disposed in the outer sleeve and movable with respect to each other responsive to reciprocation of the drive rod,
         the first shearing member having a first shearing surface, a first cutting edge having a length, and a first exterior surface, a portion of the first exterior surface adjacent the first cutting edge defining a first electrode;
         the second member having a second shearing surface, a second cutting edge, and a second exterior surface, a portion of the second shearing member adjacent the second cutting edge defining a second electrode;
      means for connecting the first and second members so that the first shearing surface moves relative to the second shearing surface through a range of motion in a scissors-like cutting action, wherein the first and second cutting edges close together for shearing tissue located therebetween, the scissor-like cutting action defining a cutting point located just distally of where the first and second cutting edges come together, the cutting point moving distally along the cutting edges where the first and second cutting edges come together through the range of motion;
      an electrically insulative material interposed between the first and second electrodes so that the first and second electrodes do not contact each other in the range of motion and so that the current passes between the first and second electrodes distal to the cutting point and not between the first and second shearing surfaces, the first and second cutting edges cutting the tissue at the cutting point;
      means for removably securing the outer sleeve to the distal end of the elongated barrel;
      drive means for coupling the first and second members to the drive rod;
      engagement means connected to the drive means for removably engaging the drive means to the drive rod; and
      means for coupling each of the first and second electrodes to a respective one of the first and second electrical contacts,
   wherein the first and second shearing members comprise an electrically conductive material, the means for connecting the first and second shearing members comprises a material that does not conduct electricity and the electrically insulative material comprises a first layer of material disposed on the first shearing surface to form substantially the entire length of the first cutting edge and the first shearing surface.

29. An instrument as defined in claim 28 wherein the first layer has a thickness selected in a range of 0.002 to 0.050 inches.

30. A detachable working end as defined in claim 28 further comprising a second layer of electrically insulative material disposed on the shearing surface of the second member to form the second cutting edge and the second shearing surface.

31. A detachable working end as defined in claim 30 wherein the first layer has a first thickness and the second layer has a second thickness and the sum of the first and second thicknesses is in a range of 0.002 and 0.050 inches.

* * * * *

UNITED STATES PATENT AND TRADEMARK OFFICE
CERTIFICATE OF CORRECTION

PATENT NO. : 5,391,166
DATED : February 21, 1995
INVENTOR(S) : Philip E. Eggers

It is certified that error appears in the above-indentified patent and that said Letters Patent is hereby corrected as shown below:

| Column | Line | |
|---|---|---|
| 1 | 8 | after "of", insert --copending,-- |
| 11 | 27 | after "124'", insert --,-- |
| 11 | 29 | after "125'", insert --,-- |
| | | after "respectively", insert --.-- |
| 11 | 33 | after "122'", insert --,-- |
| | | after "respectively", insert --.-- |

Signed and Sealed this

Thirteenth Day of August, 1996

Attest:

BRUCE LEHMAN

*Attesting Officer*  *Commissioner of Patents and Trademarks*